United States Patent
Brotz

(10) Patent No.: US 6,264,675 B1
(45) Date of Patent: Jul. 24, 2001

(54) SINGLE SUTURE STRUCTURE

(76) Inventor: Gregory R. Brotz, P.O. Box 1322, Sheboygan, WI (US) 53081

( * ) Notice: Subject to any disclaimer, the term of this patent is extended or adjusted under 35 U.S.C. 154(b) by 0 days.

(21) Appl. No.: 09/498,308

(22) Filed: Feb. 4, 2000

(51) Int. Cl.$^7$ .................................................. A61B 17/04
(52) U.S. Cl. ...................... 606/228; 606/224; 606/216; 606/223
(58) Field of Search .................. 606/216, 224, 606/228, 214

(56) References Cited

U.S. PATENT DOCUMENTS

| | | | |
|---|---|---|---|
| 3,608,095 | * 9/1971 | Barry | 606/224 |
| 3,608,539 | * 9/1971 | Miller | 606/117 |
| 5,180,385 | * 1/1993 | Sontag | 606/224 |
| 5,425,747 | * 6/1995 | Brotz | 606/228 |
| 5,584,859 | * 12/1996 | Brotz | 606/228 |
| 5,928,267 | * 7/1999 | Bonutti | 606/216 |
| 5,931,855 | * 8/1999 | Bunke | 606/228 |
| 5,989,268 | * 11/1999 | Pugsley, Jr. | 606/144 |

* cited by examiner

Primary Examiner—Gary Jackson
(74) Attorney, Agent, or Firm—William Nitkin

(57) ABSTRACT

A suture for joining the first and second sides of a cut in body tissue, such suture having an elongated body member with a needle and thread member disposed at one end thereof and retention structure which can include adhesive to retain such body member when drawn into place in the body tissue.

12 Claims, 4 Drawing Sheets

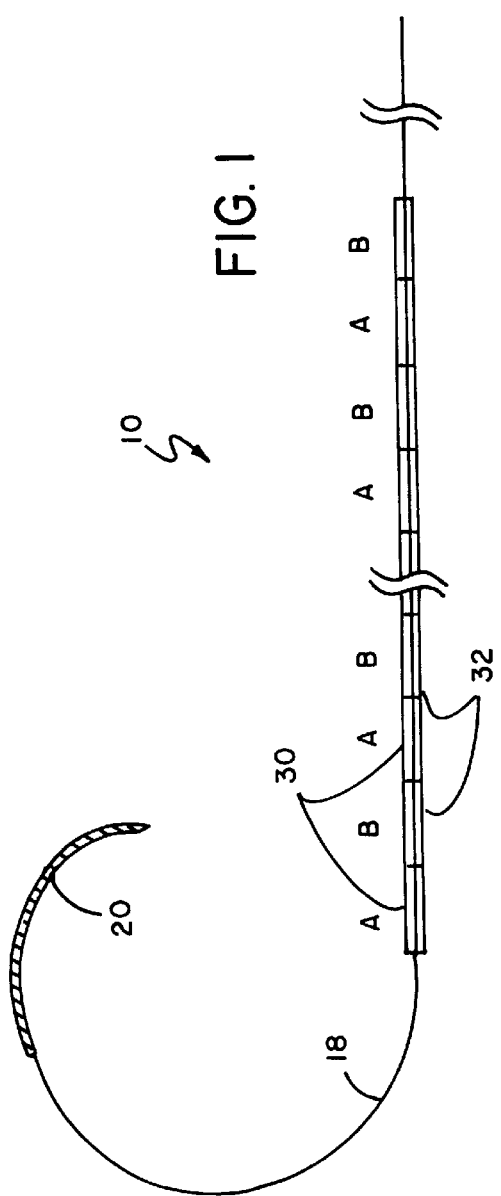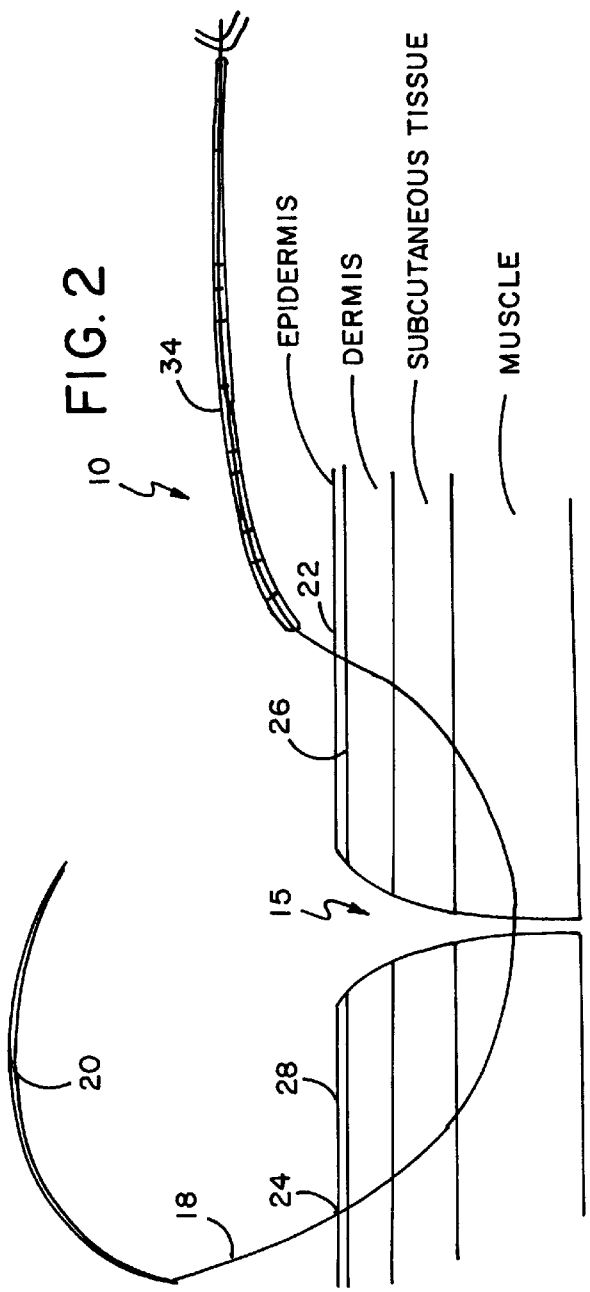

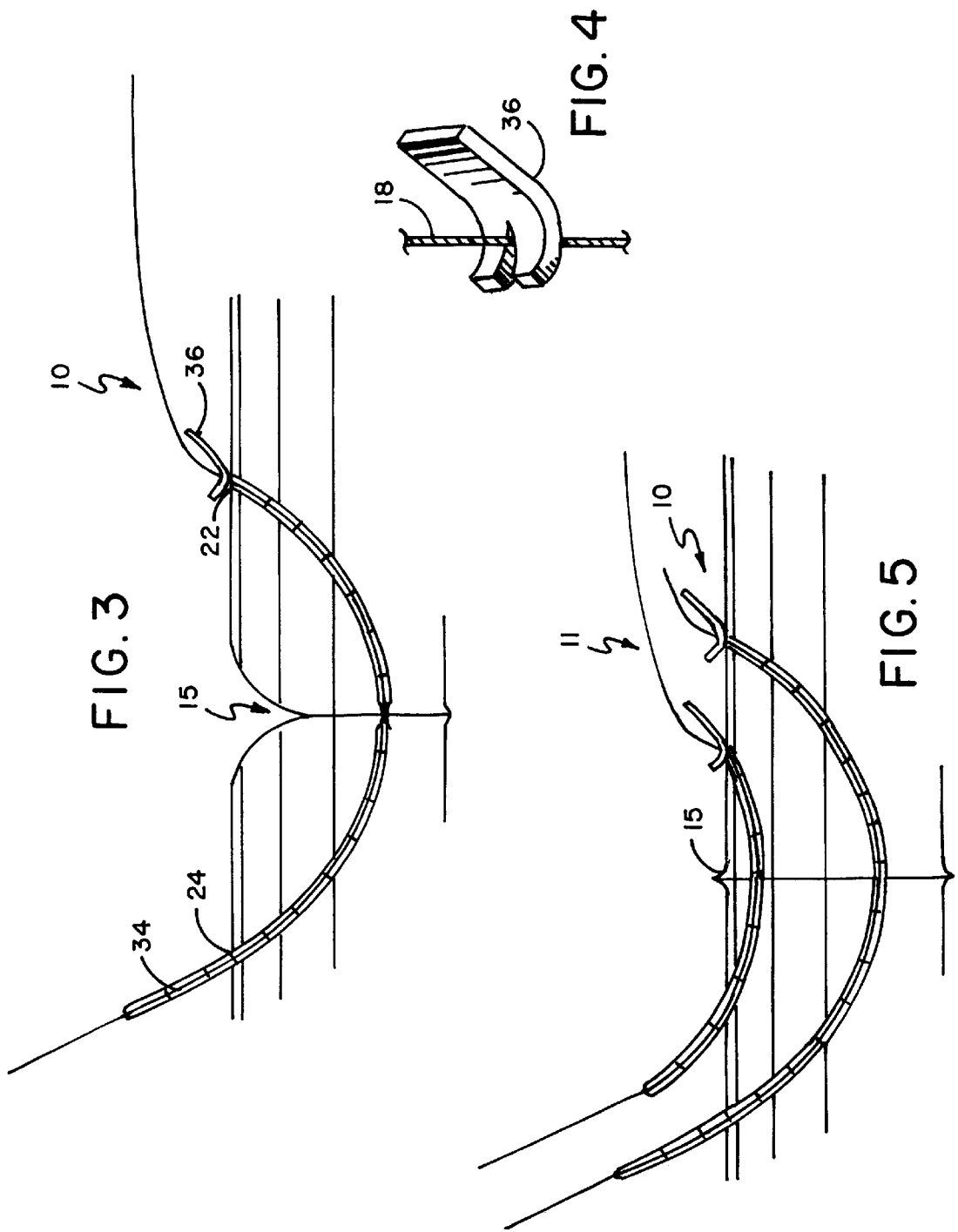

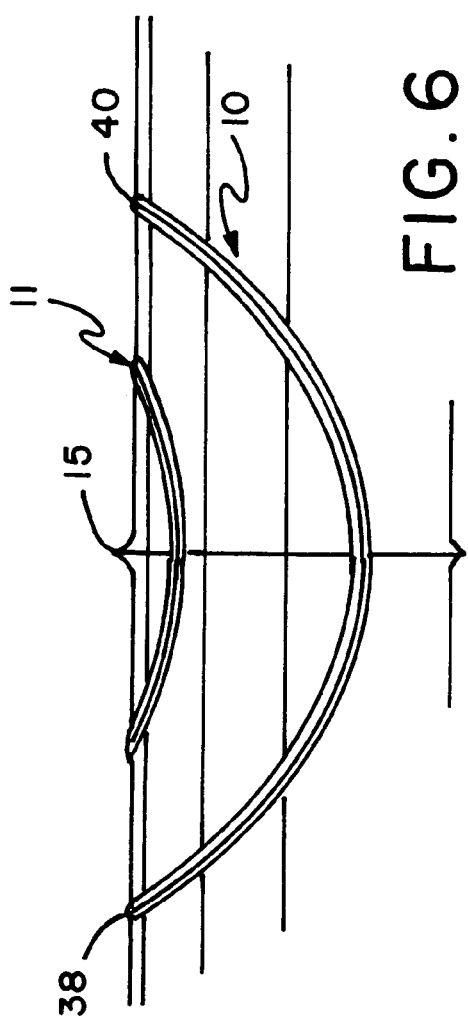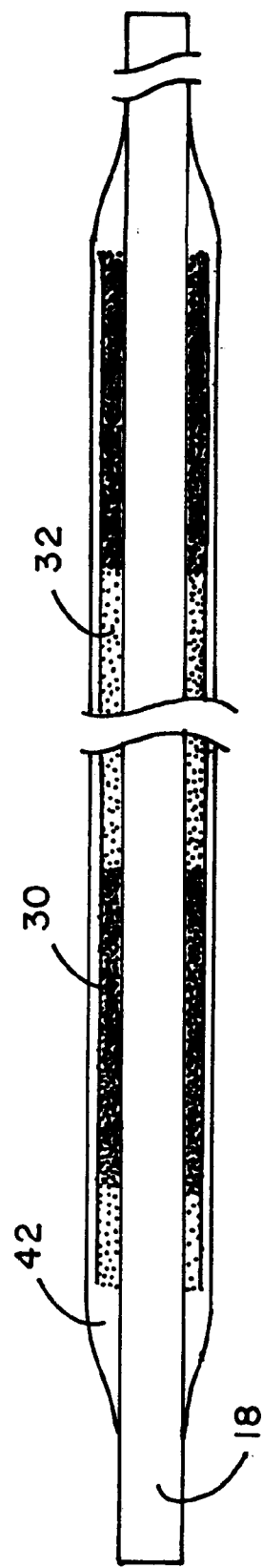

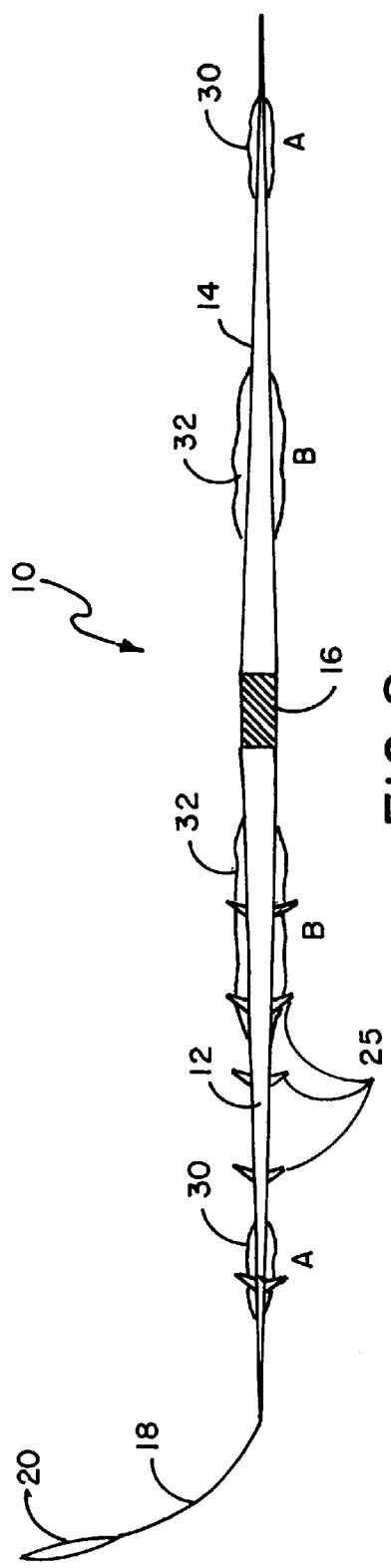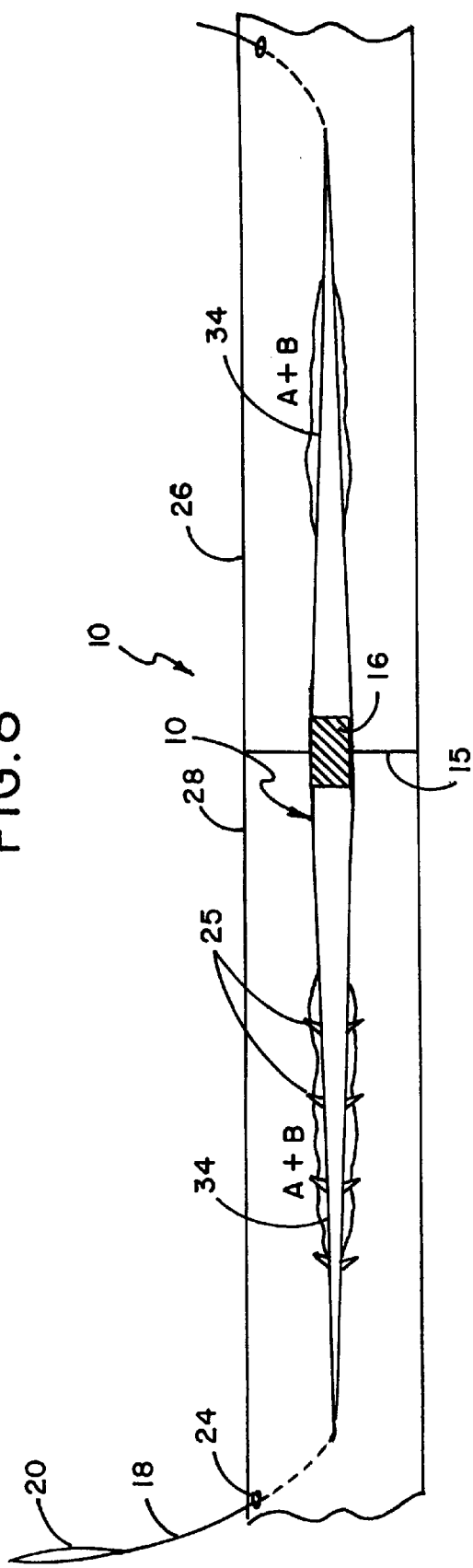

SINGLE SUTURE STRUCTURE

BACKGROUND OF THE INVENTION

1. Field of the Invention

The device of this invention resides in the area of sutures and fasteners for closing the two sides of an incision or cut in human skin or other body tissue and more particularly relates to a suture having adhesive thereon in some embodiments with a stop member and in other embodiments being a device having a central body member from which extend lateral members, each with body tissue retention means thereon such as barbs and/or adhesive, which lateral members are pulled laterally through a cut to join the two sides of the cut together.

2. Description of the Prior Art

Sutures for closing incisions or wounds are well known in the prior art. Such sutures or ligatures are often attached to the shank end of a needle and are utilized by physicians to make stitches to close incisions or wounds so that they may heal. Sutures are formed not only of threadlike material, but are also available as a one-piece unit combined with a needle. Sutures are available in a wide variety of monofilament and braided suture material. Sutures can be formed of non-absorbable material such as cat gut, silk, nylon, polyester, polypropylene, linen, or cotton as well as bioabsorbable synthetic material such as polymers and copolymers of glycolic and lactic acid. Germicides can also be incorporated into the structure or sutures which can be retained by the suture substrate to provide long-lasting germicidal properties.

Also known in the prior art are fasteners which eliminate the need for sutures in many instances. These fasteners are commonly referred to as "staples" and are useful in joining tissue layers laterally, for example, closing wounds in skin or fascia. Such staples are dispensed by implanting devices loaded with such surgical fasteners, the use of which devices can accomplish in very short time what would take many minutes to perform by suturing. Some staples can be made of bioabsorbable materials. The use of such fasteners results in a significantly reduced loss of blood and also lowers the level of trauma to the patient. Such staples can be in the form of metal staples which have arms bent by the fastening device to hook the separated body tissue together. Staples can require the stapling apparatus to have an anvil member which must be positioned under the tissue to be stapled so that the arms of the staple can be bent inwards. Two-part fastening devices also have been used which incorporate a barbed staple, the arms of which are attached to a bottom retaining member. One drawback to employing staples requiring that a retainer member be attached to it is that there must be means for positioning such retainer member under the body tissue to be joined, and one must have access to the body tissue both from above and below the body tissue. Metal staples applied to the body must also be removed by staple extractors.

Other types of surgical fasteners include skin tacks which are used to join two sides of an incision. Such skin tacks include a barbed tip on each end of the inverted U-shaped tack, the body of which is transversely positioned across an incision or cut and the tack applied so that the barbed tips engage straight downward into the skin to hold each side of the adjacent layers of body tissue together. More recently "zippers" have been applied on each side of an incision which allow for reopening, if desired.

Applicant has invented a suture assembly having a central body member with a plurality of elongated lateral members extending from the central body member from each side thereof, each such lateral member having a plurality of barbs thereon to retain the lateral members securely in the body tissue, as described in U.S. Pat. No. 5,425,747. Applicant further developed a method of lateral member insertion utilizing shaft-like, removable insertion members which can push each lateral member into position in the tissue and which insertion member can then be removed, as described in Applicant's U.S. Pat. No. 5,584,859.

SUMMARY OF THE INVENTION

It is an object of this invention to provide an improved surgical fastener for joining skin or other body tissue such as separated by a cut or an incision.

The structure of this invention in one embodiment consists of a suture of a thread material having a needle member disposed at one end and adhesive disposed along such suture in a manner so that when drawn into body tissue, the adhesive becomes activated. In use one would insert the needle member on the surface of the skin at an entry point adjacent to the cut to be closed on the first side of the cut and draw the suture material, such as a thread member, through the body tissue and out through the first inside of the cut and then into the second inside of the cut and then up through the body tissue of the second side and then out an exit point on the surface of the second side of the cut. One would draw the needle member and attached suture thread member, pulling the portion of the thread member carrying the body-activated adhesive into the body tissue on both sides of the cut. A stop member can be inserted on the thread member which, when striking the body surface on the first side of the cut, stops the advancement of the thread member and requires further pulling of the needle member to pull the sides of the cut together while at the same time the adhesive is solvated by moisture in the body tissue and becomes active, thereby retaining the body tissue to the suture and holding the cut together. The ends of the suture thread member at the stop member and at the needle member end can be cut off once the suture has brought the two sides of the cut together. Multiple levels of sutures can be used to close deep cuts with one level of suture being above the adjacent level. In some embodiments the adhesive can have a dissolving coating. The adhesive can be a mixture activated by solvation caused by moisture within the body tissue or the adhesive can be a plurality of alternate segments of adhesive which, when mixed by solvation and pulled through the body tissue, become activated. In another embodiment the invention can consist of a central body member having first and second lateral members attached thereto, such lateral members having an inner end, an outer end, and a length and being disposed in one embodiment in the same plane parallel to and aligned with one another. In one embodiment of the invention a plurality of barb members each extends from the first lateral member at a rearwardly disposed acute angle to the central body member. Such lateral member, when inserted laterally into the skin or body tissue, can remain fixed in position because the barb members, if the skin or body tissue is moved in a direction away from the central body member, will catch the skin or body tissue and prevent such outward movement. In addition, adhesive can be used to hold the second lateral member in position along with, in some embodiments, a stop member, as described above, or adhesive can be used on both lateral members in place of the barb members. The first lateral member has a generally pointed end attached to a thread member extending to a needle member. To insert such lateral member, the needle member is manually inserted into the body tissue in one side of the cut at an insertion point, pushed through the body tissue across the cut into the body tissue in the other side of the cut and then directed out of the body tissue at an exit point such that as the needle member pulls the thread member, it pulls the attached lateral member into the body tissue where the barb members, if used, allow it to advance as the barb members are rearwardly facing. When the lateral member has reached its desired position with the central body member substantially aligned with the length of the cut, the user ceases pulling on the needle member and attached thread member and cuts off the thread member at the exit point on the surface of the skin. This procedure is carried out for each suture. If adhesive is used instead of barb members, the needle and thread are held in position until the adhesive has bonded to the body tissue. A removable stop member can apply pressure to the skin as the second lateral member completes its movement through the skin. The structure of the suture assembly and thread member of this invention can be made of bioabsorbable material so that they will dissolve gradually as the cut or incision heals. Surgical adhesives based on collagen, fibrinogen or other thrombin/fibrinogen glue formulations can be used in various coating configurations with the suture assembly of this invention. When using adhesive coatings rather than barb members to retain the suture assembly in place, it should be noted that the adhesive formulations can be placed on the lateral members. When a lateral member with such adhesive coating is inserted into the body tissue, moisture in the body tissue can have a solvating effect on the glue components which, if separately deposited thereon, become mixed together as the lateral member passes through the body tissue. In order to better retain the adhesive thereto, the suture or thread surface can be modified by ion treatments or chemical surface activating agents. The thread or lateral members can also be physically pitted or cratered to provide stronger bonding of the adhesive thereto to prevent the suture from unintentionally releasing its adhesion to the body tissue. The threads, lateral members and central body member can have an extremely narrow diameter, yet be stiff enough to be pulled into the skin or other body tissue to be joined. The structure material can not only be round in cross-section, as illustrated, but also can be flat, oval or other cross-sectional shape including being hollow and containing material. The barb members can be disposed either in a plane substantially parallel to the plane of the lateral members or, in an alternate embodiment, can be disposed not only parallelly but also perpendicularly to such plane or at other positions around the lateral members to provide for even greater retention of the suture assembly within the skin or body tissue into which the lateral members of the suture assembly of this invention are inserted. In some embodiments the lateral members can extend at various angles from the central body member and are not necessarily parallel or disposed in a straight line to one another. In such embodiments a single straight or bent lateral member can be used. Each side of the suture can be treated with adhesive, and the suture advanced subcutaneously across a cut or incision so that the central body member at its midpoint is located at the junction of the sides of such cut or incision and thereby held together with such suture.

BRIEF DESCRIPTION OF THE DRAWINGS

FIG. 1 illustrates a side view of one embodiment of the suture of this invention.

FIG. 2 illustrates a cross-sectional view of the suture of this invention being drawn through body tissue.

FIG. 3 illustrates the adhesive portion of the suture of this invention having been drawn into the body tissue, closing the cut and being stopped by a stop member.

FIG. 4 illustrates a perspective side view of a stop member.

FIG. 5 illustrates a cross-sectional view through body tissue, showing multiple levels of the sutures of this invention in place.

FIG. 6 illustrates the installed sutures of FIG. 5 with their ends cut off.

FIG. 7 illustrates an enlarged cross-sectional view through a suture having adhesive in multiple segments with a dissolving coating thereover.

FIG. 8 illustrates a side cross-sectional view of one embodiment of the suture of this invention having a central body member and first and second lateral members.

FIG. 9 illustrates a side cross-sectional view of the suture of FIG. 8 showing it in position holding the sides of a cut together.

DESCRIPTION OF THE PREFERRED EMBODIMENT(S)

FIG. 1 illustrates a side view of one embodiment of suture 10 of this invention which is comprised of thread member 18 on which is coated in segments adhesive part A 30 and adhesive part B 32. Thread member 18 is attached to the shank of needle member 20. As seen in FIG. 2 needle member 20 is entered at insertion point 22 and drawn through the body tissue and out the first side 26 of cut 15 and into the second side 28 of cut 15. It is then drawn up through the body tissue through exit point 24. As seen in FIG. 3 one then draws the suture until the adhesives are in place on both sides of the tissue. A removable stop member 36 strikes the skin at insertion point 22, thereby causing pressure when the suture is pulled to close cut 15. If cut 15 does not close all the way to the skin surface, then a second suture 11, as seen in FIG. 5, can be utilized above the first suture to close the balance of cut 15. In FIG. 6 the adhesives, having been activated on the sutures, hold the body tissue in place around closed cut 15 and the first and second ends 40 and 38 are created by cutting off any protruding suture material.

FIG. 7 illustrates an enlarged cross-sectional side view of the suture of this invention wherein thread member 18 has the first part adhesive 30 and second part of adhesive 32 unmixed and covered with a dissolving coating 42 which can be made of a starch or sugar material or other inert material that will dissolve when exposed to body fluids. Such coatings are helpful when using adhesives that are fast-acting so as to provide time for the suture to be drawn into position in both sides of the cut before the coating dissolves and the adhesive is activated.

FIG. 8 illustrates a side cross-sectional view of another embodiment of suture 10 of this invention having first and second lateral members 12 and 14, each of said lateral members having an inner end connected to central body member 16. Attached to the outer end of first lateral member 12 or formed contiguously therewith is thread member 18. Thread member 18 can be made of bioabsorbable material similar to that of the rest of the suture structure. Attached to the other end of thread member 18 is needle member 20 which is attached at its shank to thread member 18. In use as in the previous embodiment, needle member 20 is held by the user and inserted into the first side of the cut at insertion point 22, as seen in FIG. 9. Needle member 20 can be straight or curved and is inserted into one side of the cut at insertion point 22 and is drawn through the body tissue across cut 15 to be pulled out at exit point 24 within second side 26 of the cut. The needle member is then pulled, drawing thread member 18 through the cut from insertion point 22 to where it passes out through exit point 24 and draws lateral member 12 into the body tissue. If barb members 25 are provided on first lateral member 12, it advances but cannot be retracted therefrom because of barb members 25 catching on the body tissue. The needle and thread members attached to lateral member 12 can be pulled so as to cause lateral member 12 to be pulled into second side 26 of cut 15 such that the first and second sides of cut 15 can be then positioned around central body member 16. When the lateral members are embedded within both sides of the cut such that the sides of the cut surround central body member 16, as seen in FIG. 8, thread member 18 can be cut off at exit point 24, and the suture is then installed.

Although a surgical incision is illustrated in the Figures, the suture assembly of this invention can also be used to fasten the irregular sides of a cut or accidental wound. In the embodiment with a central body member, such central body member can be flexible to bend to accommodate any irregularities in the shape of the cut or it can be very small with the lateral members not only in line with one another but in other embodiments extending at angles to one another therefrom. The lateral members, although shown straight, can also be curved. The suture of this invention is shown substantially enlarged in these views, but its size can vary depending on several factors such as the extent of the cut, the type of body tissue to be joined, the location of the cut, etc. The suture assembly can be made of bioabsorbable material which is well known in the prior art and should have sufficient stiffness so as to be able to be laterally pulled into the skin or body tissue. The lateral members can have flexibility as long as the barb members, if used, are rigid and the lateral members do not stretch. The central body member can be rigid or have flexibility. Surgical adhesives can be used to hold the lateral members in position and in closure of the cut or incision. In all embodiments of the suture of this invention the thread member, the central body member and the lateral members can be of any desired length and they can be formed as a single integral member. Barb members 25, if used, can be either molded in a barb-like shape or can be formed from acute angular cuts made directly in the bioabsorbable material of the lateral member with such cut portions pushed outward and separated away from the lateral member. The barb members, in one embodiment, can be formed parallel to the plane of the lateral members. The shaft of the lateral members and the central body member in a preferred embodiment can be round in cross-section but also can be of other shapes, as discussed above.

The suture member of this invention can be made of a single piece of material, as seen in FIG. 1. If the suture is of the type having a central junction area 16, such area 16 can be disposed at the incision, with first lateral side 12 inserted into first side 26 of the incision and second lateral side 14 inserted into the second side 28 of the incision, as seen in FIG. 9. The single suture structure of this invention can be held in place by barb members on one side, as described above, and the suture pulled into place by its attached needle and thread. In the embodiment illustrated in FIGS. 1–7, the suture member is held in place by an adhesive coating instead of barb members. In some embodiments, as seen in FIG. 8, the adhesive can be a two-part adhesive with one part A disposed on the outer portion of a lateral side and the second part B disposed on an inner portion of the lateral side closer to the central junction such that as the lateral side moves into the body tissue, the adhesive on its outer portion is forced by the body tissue toward the central junction and mixes with the second part of the adhesive on the inner portion of that side which mixing causes the adhesive to be activated, thereby adhering the side within body tissue. In some embodiments, as seen in FIG. 9, the adhesive parts A and B can be mixed together forming dry mixture 34 on the lateral members. In another embodiment the adhesives can be deposited in discrete segments of alternating parts, such as seen in FIG. 1. Depending on the adhesive, the length of the segments may vary including having segments of some parts of the adhesive being of greater length than others. As seen in FIG. 1 the part A adhesive 30 can be alternated in short, equal-length segments with part B adhesive 32. In another embodiment as seen in FIG. 8, a part A adhesive 30 which can be a dry or gel-phase thrombin, can be coated onto the outer portion of each lateral side and a part B adhesive 32, which can be a dry or gel-phase fibrinogen, can be coated onto the inner side of each lateral member. In use, for example, as the lateral member is inserted into the tissue, the moisture present in the tissue solvates the thrombin and the fibrinogen as the lateral member is pulled through the body tissue. As the inner half of the lateral member with the fibrinogen coating enters the insertion hole, it also solvates and mixes with the thrombin which was deposited there as the outer portion of the lateral member passed therethrough, thereby mixing with the solvated thrombin and causing the glue formation 34, as seen in FIG. 9, to become activated and adhering the suture in place. Other single component glues or dual-mixable adhesives can be utilized instead of fibrinogen and thrombin; and the fibrinogen and thrombin, if used, can be deposited alternatively on the inner or outer sides of the lateral member or can be alternatively disposed thereon in segments or as a mixture. Further, such adhesive components can be coated in the same manner onto the thread member so that as it passes through the body tissue, it leaves first one adhesive component which is then mixed with the second, thereby activating the adhesive to aid in holding the suture member in place or, if a mixture is used, it is activated by the fluid in the body tissue. Although the figures illustrate a single, curved suture member, it should be noted that the suture member of FIGS. 1 and 2 can also be straight, as seen in FIG. 9, or bent in various directions, to supply a single subcutaneous "stitch." The structure of the suture member in some embodiments can be hollow and contain medicine or even arterial stem cells to help reestablish a new blood supply.

In some instances the suture member of this invention can be utilized to secure soft tissue structure to bone. In such cases drill holes can be made in the bone sufficient to allow passage of the needle and thread member of this invention to be drawn therethrough and to pull the suture therein. In some cases there is a need to allow for movement of the body part during healing so that the suture assembly can be made of appropriate materials to provide for sufficient flexibility and elasticity, especially when reattaching soft tissue, such as tendons and ligaments, to bone. Appropriate resorbable materials are known for this purpose that work well as suture anchors and that do not leave much remnant suture material which would otherwise weaken the structure.

Although the present invention has been described with reference to particular embodiments, it will be apparent to those skilled in the art that variations and modifications can be substituted therefor without departing from the principles and spirit of the invention.

I claim:

1. A suture for joining the first and second sides of a cut defined in body tissue, comprising:
   an elongated body member having first and second ends;
   a needle member disposed at said first end of said body member; and adhesive material disposed on said body member, said adhesive material adapted to be activated when drawn into said body tissue.

2. The suture of claim 1 further including means to stop the advancement of said body member in said body tissue when said adhesive material is positioned within said body tissue.

3. The suture of claim 1 wherein said adhesive material is a multiple-part adhesive activated by solvation within body tissue.

4. The suture of claim 2 wherein said adhesive material is activated by the solvation of the body tissue.

5. The suture of claim 3 further including a dissolvable coating disposed on said adhesive material.

6. The suture of claim 4 further including a dissolvable coating disposed on said adhesive material.

7. A suture assembly for lateral insertion in body tissue, said body tissue having a cut defined therein, said cut having a length and having first and second sides, said suture assembly for joining said first and second sides of said cut at a junction formed along said length of said cut, comprising:

a central body member having first and second sides;

a first lateral member having a first end and a second end, said second end disposed on said first side of said central body member;

a second lateral member disposed on said second side of said central body member;

means to pull said first lateral member through said first side of said cut into said second side of said cut for pulling said sides of said cut together; and means to retain said suture assembly in said body tissue.

8. The suture assembly of claim 7 wherein said means to pull said first lateral member comprises a thread member having first and second ends, said second end disposed at said first end of said first lateral member and a needle disposed at said first end of said thread member.

9. The suture assembly of claim 8 wherein said means to retain said suture assembly in said body tissue comprises an adhesive disposed on said first and second lateral members, said adhesive activated when said suture assembly is pulled into said body tissue.

10. The suture assembly of claim 9 further including a dissolvable coating disposed over said adhesive.

11. The suture assembly of claim 8 wherein said means to retain said suture assembly in said body tissue further includes a plurality of barb members disposed on said first lateral member.

12. The suture assembly of claim 11 further including body tissue-activated adhesive disposed on said lateral members.

* * * * *